United States Patent [19]

Bussiere et al.

[11] Patent Number: 4,790,188
[45] Date of Patent: Dec. 13, 1988

[54] METHOD OF, AND AN APPARATUS FOR, EVALUATING FORMING CAPABILITIES OF SOLID PLATE

[75] Inventors: Jean F. Bussiere, St. Bruno; Cheng-Kuei Jen, Brossard; Irina D. Makarow, Rawdon, all of Canada; Brigitte Bacroix, St. Germain en Laye; Philippe H. Lequeu, La Buisse, both of France; John J. Jonas, Westmount, Canada

[73] Assignee: Canadian Patents and Development Limited, Ottawa, Canada

[21] Appl. No.: 71,857

[22] Filed: Jul. 10, 1987

[30] Foreign Application Priority Data

Jul. 18, 1986 [CA] Canada .................................. 514163

[51] Int. Cl.$^4$ ............................................ G01N 29/00
[52] U.S. Cl. ................................................ 73/597
[58] Field of Search ................................. 73/597, 579

[56] References Cited

U.S. PATENT DOCUMENTS 4,432,234  2/1984  Jones ...................................... 73/597
4,599,563  7/1986  Tiitto ...................................... 73/779

FOREIGN PATENT DOCUMENTS 0681366  8/1979  U.S.S.R. ................................ 73/597
1249436  8/1986  U.S.S.R. ................................ 73/597

OTHER PUBLICATIONS

Smith, R. T. "Stress-Induced Anisotropy in Solids-the Acousto-Elastic Effect" Ultrasonics (Jul.-Sep.) 1963.

Primary Examiner—Stewart J. Levy
Assistant Examiner—Lawrence G. Fess
Attorney, Agent, or Firm—Yoshiharu Toyooka

[57] ABSTRACT

A method of, and apparatus for, evaluating forming capabilities of metal plate by means of ultrasonic waves where the rolling direction and the density of the plate are known. The method comprises the steps of launching acoustic waves into the plate and detecting acoustic waves propagating in the plate to establish acoustic velocities in the plate along at least two different directions. Then the value of a certain plastic strain characteristic, like the average plastic strain ratio $\overline{R}$ or the planar strain ratio $\Delta R$, is determined from a previously established empirical relationship between the velocities and the value of the plastic strain ratio $R(\alpha)$.

19 Claims, 1 Drawing Sheet

METHOD OF, AND AN APPARATUS FOR, EVALUATING FORMING CAPABILITIES OF SOLID PLATE

FIELD OF THE INVENTION

This invention relates to a method of, and an apparatus for, evaluating forming capabilities of a solid plate having a cubic structure.

In particular, this invention relates to a rapid and non destructive method of, and apparatus for, determining average plastic strain ratio $\bar{R}$ and planar plastic strain ratio $\Delta R$.

BACKGROUND ART

It is known that the anisotropy of the plastic strain ratio $R(\alpha)$ is an important factor in predicting forming capabilities of metal plate. Measurement of $R(\alpha)$ is presently obtained mostly by destructive lengthy tensile testing. The testing implies that several plate samples of prescribed shape be cut out of each plate to be tested at different angles $\alpha$ with respect to the rolling direction of the plate, that strain gages be placed on each sample and then that each smaple be strained and the ratio of strains be measured according to the following relationship:

$$R(\alpha) = \frac{\epsilon_w(\alpha)}{\epsilon_t(\alpha)}$$

where $\epsilon_w(\alpha)$ is the true strain in the width direction and $\epsilon_t(\alpha)$ is the true strain in the thickness direction. The average plastic strain $\bar{R}$ and the planar plastic strain ratio $\alpha R$ are then determined from the measurements of $R(\alpha)$. Also known in the art is a compact tester for predicting metal sheet drawability (Metal Progress, June 1985, page 47). To obtain data representative of the sheet drawability, test strips are taken from each sheet at 0°, 45° and 90° to the rolling direction. In sequence, each strip is inserted into the unit's slot, and the resonant frequency is displayed on a digital readout. The value of these resonant frequencies are manipulated to obtain an average value of Young's modulus. Then the average plastic ratio is established from an empirical relationship with the Young's modulus. Also known in the art is a method of determining the average plastic strain ratio $\bar{R}$ of sheet material of known density (U.S. Pat. No. 4,432,234, Feb. 21, 1986, Jones). The patent uses $\bar{r}$ for the average plastic strain ratio. The method comprises the steps of subjecting the sheet material to mechanical vibrations, determining an elastic property of the material which is manifest as the velocity of the mechanical vibrations which are propagated through the thickness of the sheet, and determining the value of $\bar{R}$ from a previously established empirical relationship between the said elastic property and $\bar{R}$. Although all the above methods are suitable for estimating forming capabilities of metal plate, none of these methods can estimate the forming capabilities of metal plate with a high degree of precision by a rapid and non destructive technique.

There is a need for a method of, and an apparatus for, evaluating forming capabilities of a metal plate, with a degree of precision never achieved before, by a rapid and non destructive technique.

There is also a need for evaluating the angular variation of plastic strain ratio $R(\alpha)$ of a metal plate, with a degree of precision never achieved before, by a rapid and non destructive technique.

There is also a need for evaluating the average plastic strain ratio $\bar{R}$ of a metal plate, with a degree of precision never achieved before, by a rapid and non destructive technique.

There is also a need for evaluating the planar strain ratio $\Delta R$, with a degree of precision never achieved before, by a rapid and non destructive technique.

SUMMARY OF THE INVENTION

According to the present invention there is provided a rapid and non destructive method of evaluating forming capabilities of a solid plate of known density, the plate having rolling direction, comprising; launching acoustic waves in the plate; detecting acoustic waves propagating in the plate to establish acoustic velocities in the plate along at least two different directions; and determining the value of a certain plastic strain ratio characteristic from a previously established empirical relationship between the said velocities and the value of the plastic strain ratio characteristic.

An analysis of the elastic and plastic anisotropy in textured polycrystalline aggregates of metal structure formed of cubic crystal has been done.

The plastic strain ratio along a probed direction $R(\alpha)$, wherein $\alpha$ is the angle between the probed direction and the rolling direction of the plate in the plane of the plate, has been defined by the following relationship;

$$R(\alpha) = aV_L(\alpha) + bV_{SH}(\alpha) + cV_{SV}(\alpha) + dE(\alpha) + eV_{LND}^2 + fdV_{SND}^2 g dV_{SH}(\alpha) + h$$

where:
the letters a to h represent adjustable constants;
$V_L(\alpha)$ is the acoustic velocity of longitudinal waves propagating in the probed direction;
$V_{SH}(\alpha)$ is the acoustic velocity of shear waves, polarized in the plane of the plate, propagating in the probed direction;
$V_{SV}(\alpha)$ is the acoustic velocity of shear waves, polarized in a plane normal to the plane of the plate, propagating in the probed direction;
$E(\alpha)$ is the Young's modules in the probed direction;
$V_{LND}$ is the acoustic velocity of longitudinal waves propagating in a direction normal to the plane of the plate;

$$dV_{SND}^2 = \frac{(V_{S1ND}^2 - V_{S2ND}^2)}{(V_{LND}^2 + V_{S1ND}^2 + V_{S2ND}^2)}$$

wherein $V_{S1ND}$ is the acoustic velocity of shear waves, polarized in the rolling direction, propagating in a direction normal to the plane of the plate and $V_{S2ND}$ is the acoustic velocity of shear waves, polarized in a direction perpendicular to the rolling direction, propagating in a direction normal to the plane of the plate; and $$dV_{SH}(\alpha) = \frac{(V_{SH}(\alpha) - V_{SH}(o))}{V_{SH}(o)}.$$

The average plastic strain ratio $\bar{R}$, which is equivalent to $[R(o) + 2R(45) + R(90)]/4$, has been defined by the following relationship:

$$\bar{R} = a^1 \bar{V}_L + b^1 \bar{V}_{SH} + C^1 \bar{V}_{SV} + d^1 \bar{E} + e^1 V_{LND}^2 + f^1$$

where:
the letters $a^1$ to $f^1$ represent adjustable constants;

$$\overline{V}_L = \frac{(V_L(o) + 2V_L(45) + V_L(90))}{4};$$

$$\overline{V}_{SH} = \frac{(V_{SH}(o) + 2V_{SH}(45) + V_{SH}(90))}{4};$$

$$\overline{V}_{SV} = \frac{(V_{SH}(o) + 2V_{SV}(45) + V_{SV}(90))}{4}; \text{ and}$$

$$\overline{E} = \frac{(E(o) + 2E(45) + E(90))}{4}.$$

The planar strain ratio $\Delta R$, which is equivalent to $[R(o)+R(90)-2R(45)]/2$, has been defined by the following relationship;

$$\Delta R = a^{11}\Delta V_L + b^{11}\Delta V_{SH} + c^{11}\Delta V_{SV} + d^{11}\Delta E + e^{11}dV_{SND}^2 + f^{11}V_{LND}^2 + g^{11}$$

where the letter $a^{11}$ to $g^{11}$ represent adjustable constants;

$$\Delta V_L = \frac{(V_L(o) + V_L(90) - 2V_L(45))}{2};$$

$$\Delta V_{SH} = \frac{(V_{SH}(o) + V_{SH}(90) - 2V_{SH}(45))}{2};$$

$$\Delta V_{SV} = \frac{(V_{SV}(o) + V_{SV}(90) - 2V_{SV}(45))}{2}; \text{ and}$$

$$\Delta E = \frac{(E(o) + E(90) - 2E(45))}{2}.$$

It will be appreciated that the plates, concerned by the present invention, have a thickness varying from several microns to tens of centimeters.

Further, according to the present invention there is provided a rapid and non destructive method of evaluating forming capabilities of a metal plate of known density, the plate having a rolling direction, wherein the plastic strain chracteristic determined is the average plastic strain rato $\overline{R}$.

Further, according to the present invention there is provided a rapid and non destructive method of evaluating forming capabilities of a metal plate of known density, the plate having a rolling direction, wherein the plastic strain characteristic determined is the plastic strain ratio along a probed direction $R(\alpha)$.

Further, according to the present invention there is provided a rapid and non destructive method of evaluating forming capabilities of a metal plate of known density, the plate having a rolling direction, wherein the plastic strain characteristic determined is the planar strain ratio $\Delta R$.

Further, according to the present invention there is provided an apparatus for rapidly and non destructively evaluating fomring capabilities of a metal plate, comprising: acoustic wave launching/detecting system for launching and detecting acoustic waves in the plate along at least two different directions, the launching-/detecting system having several transducers and the distance between some of the said transducers is known to determine acoustic velocities in the plate along at least two different directions; and computer means, connected to the launching/detecting system, for establishing acoustic velocities in the plate along at least two different directions and for determining a plastic strain characteristic from a previously established empirical relationship between the said velocities and the plastic strain characteristic.

BRIEF DESCRIPTION OF THE DRAWINGS

In the accompanying drawings which illustrate, by way of example, an embodiment of the present.

DETAILED DESCRIPTION OF DRAWINGS

Figure 1:
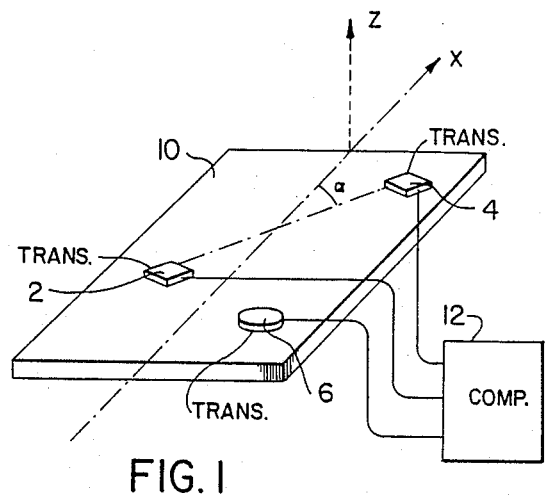
FIG. 1 shows a schematic view of an apparatus for rapidly and non destructively evaluating forming capabilities of a metal plate in a working relationship with the plate.

In FIG. 1, there is shown an apparatus for rapidly and non destructively evaluating forming capabilities of a metal plate in working relationship with the plate 10.

The apparatus comprises an acoustic wave launching/detecting system for launching and detecting acoustic waves in the plate 10 of known density along different directions. The launching/detecting systems comprises several transducers 2, 4, and 6. The distance between the transducers 2 and 4 is known so that it is possible to determine the velocity of the acoustic waves propagating in the plane of the plate 10 between the transducers 2 and 4. It is also possible to determine the velocity of acoustic waves propagating throughout the thickness of the plate 10 with transducer 6 by a pulse echo technique if the thickness of the plate 10 is known.

A computerized system 12 (which is shown in more detail in FIG. 2) is connected to the transducers 2, 4 and 6. The computerized system 12 establishes velocities of acoustic waves propagating in the plate 10 along different directions and determines the value of a plastic strain characteristic from a previously established empirical relationship between the velocities and the plastic strain characteristic. The value of the plastic strain characteristic is indicative of the forming capabilities of the plate.

The axis x indicates the rolling direction of the plate and the axis z indicates the direction normal to the plane of the plate.

The transducers 2 and 4 are used to launch and detect acoustic waves propagating in the plane of the plate. The angle $\alpha$ is indicative of the probed direction, the angle $\alpha$ is defined by the axis x and an axis passing by the two transducers 2 and 4 as shown.

The transducers 2 and 4 are selected with respect to the propagation mode and polarization wanted. It will be appreciated that more than one pair of transducers can be used to obtain different propagation modes, different polarizations or different orientation so that velocities of different acoustic waves propagating in the plane of the plate can be determined simultaneously. A pair of transducers can also be rotated with an adequate rotary apparatus (not shown) so that velocity of acoustic waves in the plane of the plate can be determined in different probed directions. The transducer 6 is used to launch and detect acoustic waves propagating throughout the thickness of the plate by a pulse echo technique. The transducer 6 is also selected with respect to the propagation mode and polarization wanted. It will be appreciated that more than one transducer, using the pulse echo technique, can be used with a different propagation mode or a different polarization so that the velocity of different acoustic waves propagating throughout the thickness of the plate can be determined simultaneously.

Figure 2:
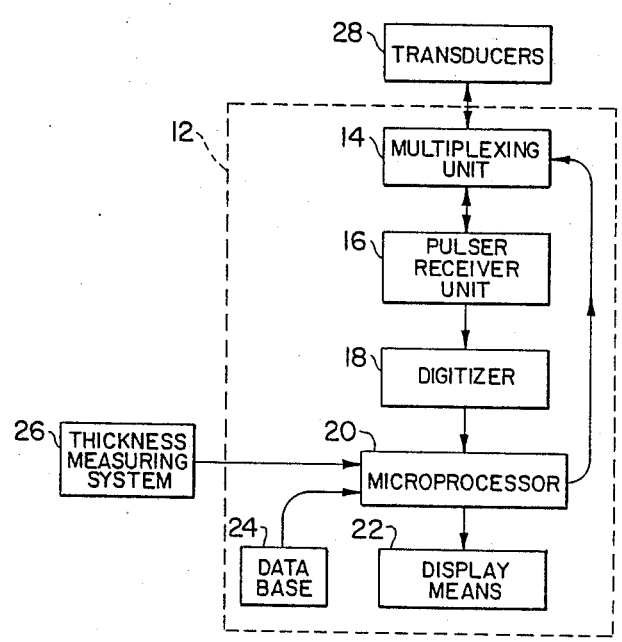
FIG. 2 shows the computerized system of FIG. 1 in more detail.

In FIG. 2, there is shown the computerized system 12 of FIG. 1 in more detail and a thickness measuring system.

The computerized system 12 comprises a multiplexing unit 14, a pulser receiver unit 16, a digitizer 18, a microprocessor 20, a data base 24 and display means 22.

The transducers 28, that launch and detect acoustic waves from the plate, are connected to the multiplexing unit 14 which selects them in sequence. The multiplexing unit 14 is connected to the input of the pulse receiver unit 16.

The output of the pulser receiver unit 16 is sent to the microprocessor 20 via the digitizer 18. A thickness measuring system 26, that measures the thickness of the plate, as well as a data base 24 are connected to the microprocessor 20.

The microprocessor 20 establishes velocities of acoustic waves propagating in the plate along at least two different directions with signals received from the digitizer 18, information taken in the data base 24 and information received from the thickness measuring system 26 if the velocity throughout the thickness of the plate is needed. Then the value of a plastic strain characteristic such as the plastic strain ratio in the probed direction $R(\alpha)$, the averge plastic strain ratio $\bar{R}$ or the planar plastic strain ratio $\Delta R$ is determined from a previously established empirical relationship between the velocities and the desired plastic strain characteristic.

In operation, the apparatus shown in FIGS. 1 and 2 may carry out a rapid and non destructive method of evaluating forming capabilities of a solid plate 10 of known density, the plate 10 having a rolling direction, comprising;

launching acoustic waves into the plate 10;

detecting acoustic waves propagating in the plate 10 to establish acoustic velocities in the plate along at least two different directions; and determining the value of certain plastic strain characteristic from a previously established empirical relationship between the said velocities and the value of the plastic strain characteristic.

It has been found that the forming capabilities of a metal plate having a cubic structure can be evaluated, according with the method of the present invention wherein the average plastic strain ratio $\bar{R}$ is determined, by establishing one of the following set of velocities;

$V_{SH}(o)$, $V_{SH}(45)$, $V_{SH}(90)$, and $V_{LND}$, or $V_{SV}(o)$, $V_{SV}(45)$, $V_{SV}(90)$, $V_L(o)$, $V_L(45)$ and $V_L(90)$, or $V_{SH}(o)$, $V_{SH}(45)$, $V_{SH}(90)$, $V_{SV}(o)$, $V_{SV}(45)$ and $V_{SV}(90)$, or $V_{SV}(o)$, $V_{SV}(45)$, $V_{SV}(90)$ and $V_{LND}$, or $V_L(o)$, $V_L(45)$, $V_L(90)$, $V_{SH}(o)$, $V_{SH}(45)$, $V_{SH}(90)$, $V_{SV}(o)$, $V_{SV}(45)$ and $V_{SV}(90)$, or $V_{SH}(o)$, $V_{SH}(45)$, $V_{SH}(90)$ and $V_{LND}$.

It will be appreciated that all of the velocities of a set of velocities do not have to be actually measured in the plate, some velocities of a certain set can be mathematically established from another measured velocity of the same set.

It has been also found that forming capabilities of a metal plate having a cubic structure can be evaluated, according with the method of the present invention wherein the plastic strain ratio along a probed direction $R(\alpha)$ is determined, by establishing one of the following set of velocities:

$V_{SV}(\alpha)$, $V_{SH}(\alpha)$, $V_{LND}$, $V_{SIND}$, and $V_{S2ND}$, or $V_{SH}(\alpha)$, $V_{SH}(o)$, $V_{SV}(\alpha)$, $V_{LND}$, $V_{SIND}$, and $V_{S2ND}$, or $V_L(\alpha)$, $V_{SH}(\alpha)$, $V_{SH}(o)$, $V_{LND}$, $V_{SIND}$, and $V_{S2ND}$.

It has been also found that the forming capabilities of a metal plate having a cubic structure can be evaluated, according with the method of the present invention wherein the planar plastic strain ratio $\Delta R$ is determined, by establishing one of the following set of velocities:

$V_L(o)$, $V_L(45)$, $V_L(90)$, $V_{LND}$, $V_{SIND}$, and $V_{S2ND}$, or $V_{SV}(o)$, $V_{SV}(45)$, $V_{SV}(90)$, $V_{SH}(o)$, $V_{SH}(45)$, $V_{SH}(90)$, $V_{LND}$, $V_{SIND}$ and $V_{S2ND}$, or $V_{SV}(o)$, $V_{SV}(45)$, $V_{SV}(90)$, $V_L(o)$, $V_L(45)$ and $V_L(90)$, or $V_{SH}(o)$, $V_{SH}(45)$, $V_{SH}(90)$, $V_{SIND}$, $V_{S2ND}$ and $V_{LND}$.

It will be appreciated that the degree of precision obtained in evaluating the forming capabilities of a solid plate depends on the material texture of the plate.

It will be also appreciated that it is within the scope of the present invention to evaluate the forming capabilities of a metal plate with the method of the present invention wherein the plastic strain characteristic established is the angular variation of yield strength $[Sy(\alpha)/Sy(o)]$.

What is claimed is:

1. A rapid and non destructive method of evaluating forming capabilities of a solid plate of known density, the plate having a rolling direction, comprising; launching acoustic waves into the plate; detecting acoustic waves propagating in the plate to establish acoustic velocities in the plate along at least two different directions; and determining the value of a certain plastic strain characteristic from a previously established empirical relationship between the said velocities and the value of the plastic strain characteristic.

2. A method as defined in claim 1 wherein:
   the plastic strain characteristic is the average plastic strain ratio $\bar{R}$; and
   the acoustic velocities are established in at least three directions comprising the rolling direction, a second direction forming an angle of 45° with the rolling direction in the plane of the plate and a third direction forming an angle of 90° with the rolling direction in the plane of the plate.

3. A method as defined in claim 2 wherein the acoustic velocities established are:
   the acoustic velocities of shear waves, polarized in the plane of the plate $V_{SH}$, propagating in the three directions; and
   the acoustic velocity of longitudinal waves propagating in a direction normal to the plane of the plate $V_{LND}$.

4. A method as defined in claim 2 wherein the acoustic velocities are:
   the acoustic velocities of shear waves, polarized in a plane normal to the plane of the plate $V_{SV}$, propagating in the three directions; and
   the acoustic velocities of longitudinal waves $V_L$ propagating in the three directions.

5. A method as defined in claim 2 wherein the acoustic velocities established are:
   the acoustic velocities of shear waves, polarized in the plane of the plate $V_{SH}$, propagating in the three directions; and
   the acoustic velocities of shear waves, polarized in a plane normal to the plane of the plate $V_{SV}$, propagating in the three directions.

6. A method as defined in claim 2 wherein the acoustic velocities established are:

the acoustic velocities of shear waves, polarized in a plane normal to the plane of the plate $V_{SV}$, propagating in the three directions; and longitudinal waves propagating in a direction normal to the plane of the plate $V_{LND}$.

7. A method as defined in claim 2 wherein the acoustic velocities established are:

the acoustic velocities of longitudinal waves $V_L$ propagating in the three directions;

the acoustic velocities of shear waves, polarized in the plane of the plate $V_{SH}$, propagating in the three directions; and the acoustic velocities of shear waves, polarized in a plane normal to the plane of the plate $V_{SV}$, propagating in the three directions.

8. A method as defined in claim 2 wherein the acoustic velocities are:

the acoustic velocities of shear waves, polarized in the plane of the plate $V_{SH}$, propagating in the three directions;

the acoustic velocities of shear waves, polarized in a plane normal to the plane of the plate $V_{SV}$, propagating in the three directions; and the acoustic velocity of longitudinal waves propagating in a direction normal to the plane of the plate $V_{LND}$.

9. A method as defined in claim 1 wherein the plastic strain characteristic is the plastic strain ratio along a probed direction $R(\alpha)$, the probed direction forming an angle $\alpha$ with the rolling direction in the plane of the plate.

10. A method as defined in claim 9 wherein the acoustic velocities established are:

the acoustic velocity of shear waves, polarized in a plane normal to the plane of the plate, propagating in the probed direction $V_{SV}(\alpha)$;

the acoustic velocity of shear waves, polarized in the plane of the plate, propagating in the probed direction $V_{SH}(\alpha)$;

the acoustic velocity of longitudinal waves propagating in a direction normal to the plane of the plate $V_{LND}$;

the acoustic velocity of shear waves, polarized in the rolling direction, propagating in a direction normal to the plane of the plate $V_{SIND}$; and the acoustic velocity of shear waves polarized in a direction perpendicular to the rolling direction, propagating in a direction normal to the plane of the plate $V_{S2ND}$.

11. A method as defined in claim 9 wherein the acoustic velocities established are:

the acoustic velocities of shear waves, polarized in the plane of the plate, propagating in the probed direction $V_{SH}(\alpha)$ and in the rolling direction $V_{SH}(\alpha)$;

the acoustic velocity of shear waves, polarized in a plane normal to the plane of the plate, propagating in the probed direction $V_{SV}(60)$;

the acoustic velocity of longitudinal waves propagating in a direction normal to the plane of the plate $V_{LND}$;

the acoustic velocity of the shear waves, polarized in the rolling direction, propagating in a direction normal to the plane of the plate $V_{SIND}$; and the acoustic velocity of shear waves, polarized in a direction perpendicular to the rolling direction, propagating in a direction normal to the plane of the plate $V_{S2ND}$.

12. A method as defined in claim 9 wherein the acoustic velocities established are:

the acoustic velocity of longitudinal waves propagating in the probed direction $V_L(\alpha)$;

the acoustic velocities of shear waves, polarized in the plane of the plate, propagating in the probed direction $V_{SH}(\alpha)$ and the rolling direction $V_{SH}(o)$;

the acoustic velocity of longitudinal waves propagating in a direction normal to the plane of the plate $V_{LND}$;

the acoustic velocity of shear waves, polarized in the rolling direction, propagating in a direction normal to the plane of the plate $V_{SIND}$; and the acoustic velocity of shear waves, polarized in a plane perpendicular to the rolling direction, propagating in a direction normal to the plane of the plate $V_{S2ND}$.

13. A method as defined in claim 1 wherein:

the plastic strain characteristic is the planar strain ratio $\Delta R$; and the acoustic velocities are established in at least three directions comprising the rolling direction, a second direction forming an angle of 45° with the rolling direction in the plane of the plate and a third direction forming an angle of 90° with the rolling direction in the plane of the plate.

14. A method as defined in claim 13 wherein the acoustic velocities established are:

the velocity of longitudinal waves propagating in the three directions $V_L$;

the acoustic velocity of longitudinal waves propagating in a direction normal to the plane of the plate $V_{LND}$;

the acoustic velocity of shear waves, polarized in the rolling direction, propagating in a direction normal to the plane of the plate $V_{SIND}$; and the acoustic velocity of shear waves, polarized in a direction perpendicular to the rolling direction, propagating in a direction normal to the plane of the plate $V_{S2ND}$.

15. A method as defined in claim 13 wherein the acoustic velocities established are:

the acoustic velocities of shear waves, polarized in a plane normal to the plane of the plate $V_{SV}$, propagating in the three directions;

the acoustic velocities of shear waves, polarized in the plane of the plate $V_{SH}$, propagating in the three directions;

the acoustic velocity of longitudinal waves propagating in a direction normal to the plane of the plate $V_{LND}$;

the acoustic velocity of shear waves, polarized in the rolling direction, propagating in a direction normal to the plane of the plate $V_{SIND}$; and the acoustic velocity of shear waves, polarized in a direction perpendicular to the rolling direction, propagating in a direction normal to the plane of the plate $V_{S2ND}$.

16. A method as defined in 13 wherein the acoustic velocities established are:

the acoustic velocities of shear waves, polarized in a plane normal to the plane of the plate $V_{SV}$, propagating in the three direction; and acoustic velocities of longitudinal waves $V_L$ propagating in the three directions.

17. A method as defined in claim 13 wherein the acoustic velocities established are:

the acoustic velocities of shear waves, polarized in the plane of the plate $V_{SH}$, propagating in the three directions;

the acoustic velocity of shear waves, polarized in the rolling direction, propagating in a direction normal to the plane of the plate $V_{S1ND}$;

the aromatic velocity of shear waves, polarized in a direction perpendicular to the rolling direction, propagating in a direction normal to the plane of the plate $V_{S2ND}$; and the acoustic velocity of longitudinal waves propagating in a direction normal to the plane of the plate $V_{LND}$.

18. An apparatus for rapidly and non destructively evaluating forming capabilities of a solid plate, comprising:

acoustic wave launching/detecting system for launching and detecting acoustic waves in the plate along at least two different directions, the launching/detecting system having several transducers and the distance between some of the said transducers is known to determine acoustic velocities in the plate along at least two different directions;

computer means, connected to the lauching/detecting system, for establishing velocities of acoustic waves propagating in the plate along at least two different directions and for determining the value of a plastic strain characteristic from a previously established empirical relationship between the said velocities and the value of the said plastic strain characteristic; and display means for displaying the value of the said plastic strain characteristic which is indicative of the forming capabilities of the plate.

19. An apparatus as defined in claim 18, further comprising a thickness evaluating means, connected to the computer means, for generating a thickness signal responsive to the thickness of the plate.

* * * * *